US011110232B2

(12) United States Patent
Hsieh et al.

(10) Patent No.: US 11,110,232 B2
(45) Date of Patent: Sep. 7, 2021

(54) NEBULIZATION GENERATING APPARATUS

(71) Applicant: MicroBase Technology Corp., Taoyuan (TW)

(72) Inventors: Shu-Pin Hsieh, Taoyuan (TW); Yi-Tong Chen, Taoyuan (TW); Ting-Kai Tsai, Taoyuan (TW); Po-Chuan Chen, Taoyuan (TW); Chih-Wei Lu, Taoyuan (TW)

(73) Assignee: MicroBase Technology Corp., Taoyuan (TW)

(*) Notice: Subject to any disclaimer, the term of this patent is extended or adjusted under 35 U.S.C. 154(b) by 362 days.

(21) Appl. No.: 15/653,530

(22) Filed: Jul. 19, 2017

(65) Prior Publication Data

US 2018/0021528 A1    Jan. 25, 2018

Related U.S. Application Data

(60) Provisional application No. 62/364,309, filed on Jul. 19, 2016.

(51) Int. Cl.
*A61M 11/00* (2006.01)
*B05B 15/18* (2018.01)
(Continued)

(52) U.S. Cl.
CPC ...... *A61M 11/005* (2013.01); *A61M 15/0001* (2014.02); *A61M 15/0085* (2013.01);
(Continued)

(58) Field of Classification Search
CPC ............ A61M 11/005; A61M 15/0085; A61M 15/0001; A61M 2205/0294;
(Continued)

(56) References Cited

U.S. PATENT DOCUMENTS 6,732,944 B2 * 5/2004 Litherland ........... A61M 11/005
239/102.1
2005/0034719 A1 * 2/2005 Feiner ............... A61M 15/0085
128/200.21
(Continued)

FOREIGN PATENT DOCUMENTS

CN    203842759 U    9/2014
CN    204412540 U    6/2015
(Continued)

OTHER PUBLICATIONS

Lee W. Young, PCT/US 16/17984 International search report, dated Jun. 28, 2016, ISA/US.
(Continued)

*Primary Examiner* — Annette Dixon
(74) *Attorney, Agent, or Firm* — OPES IP Consulting Co., Ltd.

(57) ABSTRACT

An aerosol generating apparatus is disclosed. The apparatus includes a liquid container, an adaptor detachably engaged with the liquid container, and a driving element accommodated by the adaptor. A perforated membrane, through which a liquid can pass through, is disposed at an exit of the liquid container. Moreover, the perforated membrane faces the driving element. The driving element includes a substrate coupled with a piezoelectric element. The substrate includes an aperture that corresponds to the perforated membrane when the liquid container and the adaptor are engaged so as to receive liquid. Moreover, when the liquid container and the adaptor are engaged, the perforated membrane is in contact with the substrate at the proximity of the aperture, which is about the substrate's center. The adaptor is configured to contact the substrate's periphery only. The resulting apparatus generates aerosol at a desired efficiency with less energy needed.

18 Claims, 10 Drawing Sheets

Figure 1A:
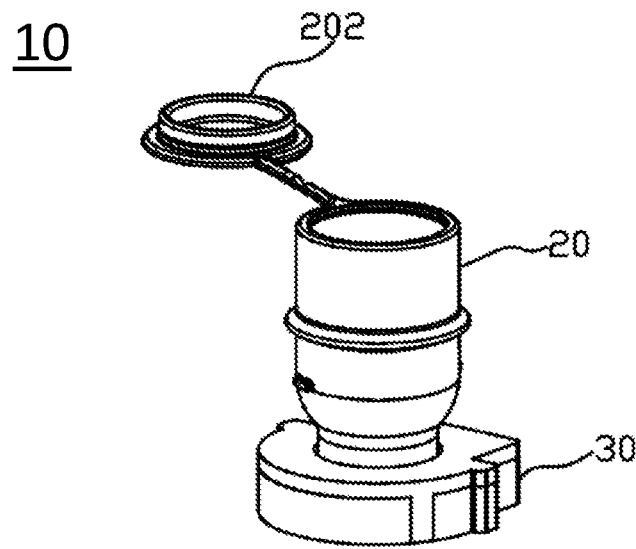

(51) Int. Cl.
*B05B 17/06* (2006.01)
*A61M 15/00* (2006.01)
*B05B 17/00* (2006.01)

(52) U.S. Cl.
CPC .......... *B05B 15/18* (2018.02); *B05B 17/0646* (2013.01); *B05B 17/0653* (2013.01); *A61M 2205/0294* (2013.01); *A61M 2205/121* (2013.01); *A61M 2205/123* (2013.01)

(58) Field of Classification Search
CPC .......... A61M 2205/123; A61M 11/001; A61M 15/00; A61M 2205/121; B05B 17/0646; B05B 1/14; B05B 1/185; B05B 15/18; B05B 17/06; B05B 17/0607; B05B 17/0653; B05B 7/2408; A61K 2039/505; A61K 39/39591; A61K 9/0078; A61P 11/00; A61P 11/02; A61P 37/02; C07K 16/00; C07K 16/1027; C07K 16/1275
See application file for complete search history.

(56) References Cited

U.S. PATENT DOCUMENTS

| | | | |
|---|---|---|---|
| 2007/0051827 A1* | 3/2007 | Shen | B05B 17/0646 239/102.2 |
| 2009/0137950 A1* | 5/2009 | Loenner | A61J 1/067 604/82 |
| 2012/0291776 A1* | 11/2012 | Van Der Mark | A61M 11/005 128/200.14 |
| 2013/0074832 A1* | 3/2013 | Gallem | A61M 11/005 128/200.14 |
| 2013/0112770 A1* | 5/2013 | Hsieh | B05B 17/0646 239/102.1 |
| 2013/0119151 A1* | 5/2013 | Moran | A61M 11/005 239/102.2 |
| 2014/0116426 A1 | 5/2014 | Mullinger et al. | |
| 2016/0119151 A1 | 4/2016 | Park et al. | |
| 2016/0158789 A1* | 6/2016 | Selby | B05B 17/0646 239/102.1 |
| 2018/0178240 A1* | 6/2018 | Anzenberger | A61M 11/005 |

FOREIGN PATENT DOCUMENTS

| | | |
|---|---|---|
| CN | 105579147 A | 5/2016 |
| CN | 105579147 A | 5/2016 |
| EP | 1762264 A1 | 3/2007 |
| EP | 2957349 A1 | 12/2015 |
| WO | WO2011083380 A1 | 7/2011 |
| WO | 2013161986 A1 | 10/2013 |
| WO | WO2016133856 A2 | 8/2016 |

OTHER PUBLICATIONS

Office Action Communication from TIPO, dated Aug. 16, 2018.
Office Action Communication from TIPO, dated Nov. 26, 2018.
Extended European search report by the EPO, dated Dec. 21, 2017.
First Office Action prepared by CNIPA, dated Nov. 5, 2019.

* cited by examiner

NEBULIZATION GENERATING APPARATUS

CROSS REFERENCE TO RELATED APPLICATION

The present application claims priority to U.S. Provisional Application Ser. No. 62/364,309 filed on Jul. 19, 2016, which is hereby incorporated by reference in its entirety. In addition, the entire disclosure in the PCT Application PCT/US16/17984 is hereby incorporated by reference.

FIELD

The present disclosure relates to an aerosol generating apparatus and more particularly to an aerosol generating apparatus with interchangeable components.

BACKGROUND

Nebulizers, also known as aerosolizer or atomizer, are used to deliver medication in fine particles/droplets to patients for inhalation. An aerosol generating module, which is a component of a nebulizer, receives liquid medicament to generate aerosol for treating a patient with respiratory conditions, such as Chronic Obstructive Pulmonary Disease (COPD). A typical aerosol generating module includes a perforated membrane and a vibratable element. One way for a vibratable element to generate vibration is through the incorporation of piezoelectric (PZT) materials. Vibration is provided to the liquid passing through the perforated membrane, thereby generating aerosolization.

A reservoir, with an internal chamber, stores the liquid medicament to be provided to the aerosol generating module. The vibratable element vibrates the perforated membrane, through which the liquid medicament travels through, to generate aerosolization. Typically, the aerosol generating module is either permanently secured to the reservoir or integrally formed with the reservoir. The aerosol generating module may be secured to the reservoir with adhesives or by other securing means. Accordingly, when the liquid medicament is depleted, the aerosol generating module, which is affixed to the reservoir, is also discarded or replaced.

Generally, the reservoir needs to be cleaned thoroughly prior to each use. The same applies to the perforated membrane. If the reservoir and/or the perforated membrane were not cleaned properly, the nebulizer may not work in subsequent use. For example, residue may form and block the perforated membrane. The vibratable element, if not cleaned adequately, may degrade fast and generate reliability and performance issues. The liquid medicament may also be contaminated due to insufficient cleaning. The above-mentioned risks can be mitigated by using a new set of aerosol generating module and reservoir for every treatment. However, it will substantially increase the patient's financial burden.

Therefore, the present disclosure aims to design a nebulizer with interchangeable and replaceable components, including liquid container, perforated membrane and vibratable element. The goal is to improve, or maintain over time, nebulization quality and efficiency, while providing patient a cost-effective treatment solution.

SUMMARY

The disclosure provides an aerosol generating apparatus having an adaptor with a driving element, and a liquid container with a perforated membrane. The driving element includes a piezoelectric element and a substrate, and the driving element is accommodated by the adaptor. The center of the substrate has an aperture and the adaptor is configured to contact the substrate at its periphery. The aperture may be proximate to the substrate's center. The liquid container has a chamber for holding a liquid medicament and an opening for releasing the liquid. The membrane is at the opening of the liquid container and corresponds to the aperture of the substrate when the liquid container and the adaptor are engaged. When engaged, the liquid medicament is supplied to the perforated membrane, which is vibrated by the driving element through the substrate. As a result, the liquid medicament passes through the perforated membrane and is nebulized.

In some embodiments, the substrate includes an inlet surface and an outlet surface opposite to the inlet surface. The inlet surface further includes a projection extending away from its face, and a through hole is configured to penetrate a structure plate at the projection. The driving element couples with and vibrates the structure plate. Particularly, when the liquid container is engaged with the adaptor, the membrane of the liquid container is in contact with the projection such that the driving element vibrates the membrane through the projection.

In some embodiments, a space is formed between the inlet surface and the membrane when the projection is in contact with the membrane. In another embodiment, the substrate further includes a planar part at the inlet surface extending annularly from the projection, and the space between the membrane and the structure plate corresponds to the planar part.

In some embodiments, the substrate is in contact, touches or abuts the adaptor. The adaptor further includes a jack for supporting and holding the substrate. This way, the substrate is securely maintained in a position relative to the adaptor to ensure accurate alignment between the substrate and membrane while the contact areas between the substrate and the adaptor are minimized. The required reliable alignment between the nebulizer components during the process of aerosol generation is then achieved.

In some embodiments, the adaptor includes at least two jacks. The jacks may be integrally formed with the adaptor. The substrate is in contact with and held by the jacks. The substrate may be attached to the at least two jacks by adhesive. Alternatively, the substrate may be directly mounted on at least two jacks without adhesive.

In some embodiments, the respective jack has a first surface extending along a direction perpendicular to the longitudinal axis of the adaptor. Accordingly, the substrate can be mounted on and in contact with the first surface. In certain embodiments, the substrate may be attached to the first surface by adhesive, such as gel.

In some embodiments, the substrate is mounted directly to the first surface without adhesive. The substrate may be considered as supported by the adaptor, at least partially. Further, a pressing force in a direction perpendicular to the first surface may be provided, from the membrane against the projection of the substrate, such that the relative position between the substrate and the adaptor is maintained. In other words, the substrate may be clamped by the first surface and the liquid container when the liquid container is engaged with the adaptor.

In some embodiments, the jack further includes a second surface along the longitudinal axis of the adaptor. The substrate may be in contact with both the first and second surfaces. Furthermore, the substrate may be adhered to the first and second surfaces, or not.

In some embodiments, the substrate has recesses at its outer periphery corresponding to the first surface and the second surface. As a result, the substrate may be fitted more firmly with the adaptor to inhibit horizontal movement. Further, a pressing force in a direction perpendicular to the substrate may be provided such that the substrate is more securely clamped by the adaptor and the container. In yet another example, the substrate may be adhered to the jacks.

In some embodiments, the distal part of the second surface is melted using hot melting adhesive process and forms an additional surface which is parallel to the first surface. The additional surface is in contact with the substrate and together with first and second surfaces, and therefore the substrate is securely fixed by the jack. All three surfaces may be in contact with the substrate. In certain embodiments, the jacks come with the three surfaces.

In some embodiments, the adaptor is configured to contact the substrate's periphery at no more than three locations. Alternatively, no more than six percent of the substrate is in contact with the adaptor so as to maximize the vibration energy transmission to the membrane or to minimize vibration energy loss.

In some embodiments, the substrate is made of metal such as stainless steel, and the jack of the adaptor is made of material other than metal, such as polymer.

In some embodiments, the adaptor includes a supporting means and an interface, and the interface is configured to receive a liquid source. The liquid source is detachably engaged with the interface of the adaptor. As a result, the aerosol generating apparatus is modularized and components including the liquid source, the perforated membrane and the piezoelectric element can be replaced when needed. The supporting means is in contact with the periphery of the substrate and is configured to maintain a space between the substrate and the adaptor when the adaptor is engaged with the liquid source.

BRIEF DESCRIPTION OF THE DRAWINGS

One or more embodiments are illustrated by way of example, and not by limitation, in the figures of the accompanying drawings, wherein elements having the same reference numeral designations represent like elements throughout. The drawings are not to scale, unless otherwise disclosed.

FIGS. 1A-1B are side views of an aerosol generating apparatus in accordance with some embodiments of the present disclosure.

FIG. 2 illustrates an exploded view of an aerosol generating apparatus 10 according to some embodiments of the present disclosure.

FIG. 3 is an exploded view of part of the aerosol generating device according to some embodiments of the present disclosure.

FIGS. 4A-4C are side views of part of an aerosol generating apparatus in accordance with some embodiments of the present disclosure.

FIGS. 5A-5B are cross-sectional views of the aerosol generating apparatus according to some embodiments of the present disclosure.

FIGS. 6A-6E are cross-sectional views of the aerosol generating apparatus in accordance with some embodiments of the present disclosure.

FIGS. 7A-7D are exemplary views of the substrate and the adaptor in accordance with some embodiments of the present disclosure.

The drawings are only schematic and are non-limiting. In the drawings, the size of some of the elements may be exaggerated and not drawn on scale for illustrative purposes. The dimensions and the relative dimensions do not necessarily correspond to actual reductions to practice of the invention. Any reference signs in the claims shall not be construed as limiting the scope. Like reference symbols in the various drawings indicate like elements.

DETAILED DESCRIPTION OF THE DISCLOSURE

The making and using of the embodiments of the disclosure are discussed in detail below. It should be appreciated, however, that the embodiments provide many applicable inventive concepts that can be embodied in a wide variety of specific contexts. The specific embodiments discussed are merely illustrative of specific ways to make and use the embodiments, and do not limit the scope of the disclosure.

Throughout the various views and illustrative embodiments, like reference numerals are used to designate like elements. Reference will now be made in detail to exemplary embodiments illustrated in the accompanying drawings. Wherever possible, the same reference numbers are used in the drawings and the description to refer to the same or like parts. In the drawings, the shape and thickness may be exaggerated for clarity and convenience. This description will be directed in particular to elements forming part of, or cooperating more directly with, an apparatus in accordance with the present disclosure. It is to be understood that elements not specifically shown or described may take various forms. Reference throughout this specification to "one embodiment" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. It should be appreciated that the following figures are not drawn to scale; rather, these figures are merely intended for illustration.

In the drawings, like reference numbers are used to designate like or similar elements throughout the various views, and illustrative embodiments of the present disclosure are shown and described. The figures are not necessarily drawn to scale, and in some instances the drawings have been exaggerated and/or simplified in places for illustrative purposes. One of ordinary skill in the art will appreciate the many possible applications and variations of the present disclosure based on the following illustrative embodiments of the present disclosure.

It will be understood that when an element is referred to as being "on" another element, it can be directly on the other element or intervening elements may be present. In contrast, when an element is referred to as being "directly on" another element, there are no intervening elements present.

It will be understood that singular forms "a", "an" and "the" are intended to include the plural forms as well, unless the context clearly indicates otherwise. Furthermore, relative terms, such as "bottom" and "top," may be used herein to describe one element's relationship to other elements as illustrated in the Figures.

It will be understood that elements described as "under" or "below" other elements would then be oriented "over" or "above" the other elements. The exemplary terms "under" or "below" can, therefore, encompass both an orientation of over and under.

Unless otherwise defined, all terms (including technical and scientific terms) used herein have the same meaning as commonly understood by one of ordinary skill in the art to which this disclosure belongs. It will be further understood that terms; such as those defined in commonly used dictionaries, should be interpreted as having a meaning that is consistent with their meaning in the context of the relevant art and the present disclosure, and will not be interpreted in an idealized or overly formal sense unless expressly so defined herein.

Figure 1B:
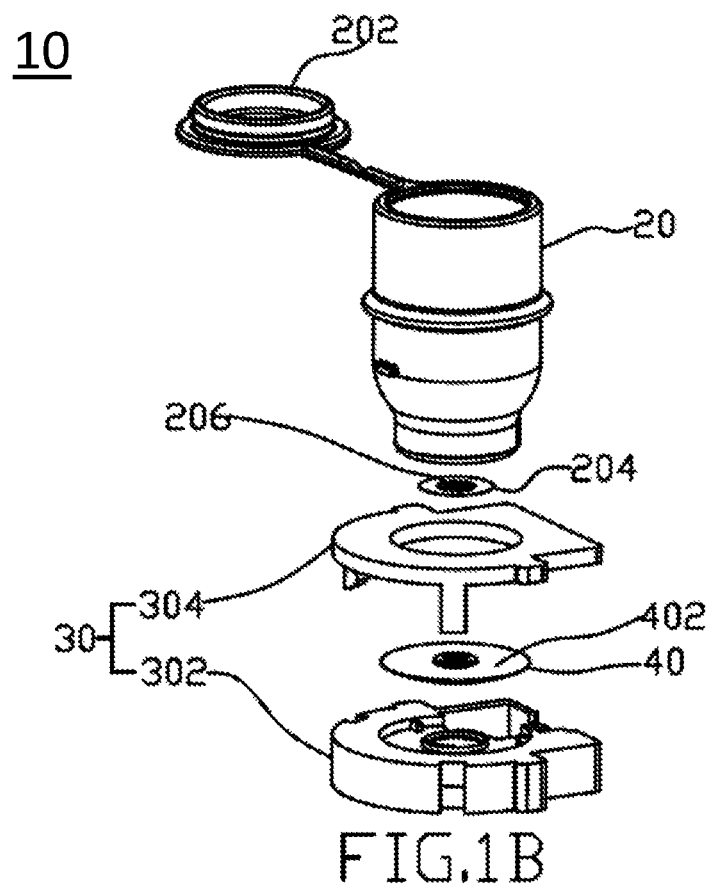

FIGS. 1A-1B are side views of an aerosol generating apparatus in accordance with some embodiments of the present disclosure.

Referring to FIG. 1A, an aerosol generating apparatus 10 is disclosed. The aerosol generating apparatus 10 includes a liquid container 20 and a corresponding adaptor 30. Here, the liquid container 20 is engaged with the adaptor 30. As will be discussed in subsequent disclosures and embodiments, the liquid container 20 and the adaptor 30 can be disengaged. As such, users are allowed to replace the liquid container 20 while continue to use the same adaptor 30. Conversely, users may replace the adaptor 30 and/or the components therein when it's damaged or after prolonged use, while continue to use the same liquid container 20.

The liquid container 20 is configured to hold a liquid medicament (not shown) or any medication suitable for aerosolization to be provided to the aerosol generating apparatus 10. The liquid container 20 may include a lid 202 covering an inlet, through which users can re-fill the liquid medicament. Alternatively, the liquid container 20 may not include such lid 202. Accordingly, users need to replace the liquid container entirely when the liquid medicament is depleted. The liquid container 20 includes an outlet opening (not shown) facing the adaptor 30. Through such opening, liquid is provided to the adaptor 30 for aerosolization.

The adaptor 30 is configured to house aerosolization components therein, which will be discussed in subsequent disclosures and embodiments. The adaptor 30 includes an inlet at one side for receiving liquid from the liquid container 20 and an outlet opposite to the inlet. Liquid enters the adaptor 30 and exits through the outlet in the form of aerosol. As such, the adaptor 30 is made of impermeable material(s). Moreover, the adaptor 30 may accommodate electric wires (not shown) for delivery of electric power to certain components therein. The impermeable material also serves to improve the durability of such electric parts.

Aerosolization is to be conducted after the liquid container and the adaptor is engaged. The relative position between the reservoir 20 and the holder 30 is fixed during aerosolization to ensure the liquid medicament is aerosolized under a controlled manner. Still, their relative position may be adjusted to configure the aerosolization rate based on different needs.

FIG. 1B illustrates the aerosol generating apparatus 10 with the liquid container 20 disengaged from the adaptor 30. Further, relevant components accommodated by the container 20 and the adaptor 30 are shown in an exploded view. Here, the liquid container 20 includes a membrane 204 at its outlet opening. At least part of the membrane 204 is porous. That is, the membrane 204 includes a plurality of orifices 206 for the liquid medicament to eject. Therefore, the membrane 204 may also be referred to as a perforated membrane. Exemplary ways of forming the orifices 206 include etching or laser drilling. The orifices 206 can also be formed by other method known to persons having ordinary skill in the art. The size of the orifices 206 is configured to substantially prevent liquid medicament from leaking. In certain embodiments, the orifices 206 are positioned around the center of the membrane 204. In some embodiments, the orifices 206 may be distributed all over the membrane 204 or at certain sections only, depending on the configuration of the rest of the components of the aerosol generating apparatus 10.

In some embodiments, the membrane 204 is made of a material flexible enough to respond to vibration, yet sturdy enough to maintain liquid from leakage or prevent contamination from outside environment. In certain embodiments, the membrane 204 is made of a macromolecular polymer of polyimide, polyethylene (PE), polypropylene (PP), polyether ether ketone (PEEK) and/or the combination thereof. When the membrane 204 is integrally formed with the liquid container 20, the two are made of the same material or same combination of materials. A separate container or vial may be added to encase the liquid container 20.

The adaptor 30 may include a body 302 and an interface 304. Together they may form a chamber for accommodating components therein. The body 302 and the interface 304 may be integrated into one single structure. Alternatively, only the body 302 is needed to accommodate elements therein and for engaging with the liquid container 20. In certain embodiments, the interface 304 may serve to mate, align and/or affix the liquid container 20 to the adaptor 30. For example, the liquid container 20 and the interface 304 may both include screw threads such that a user can screw fix the two together. A person having ordinary skill in the art would understand that other mating/aligning/affixing mechanisms may applied as long as the relative position between the liquid container 20 and the adaptor 30 can be maintained during aerosolization. If such positions are not maintained, the liquid container 20 might shift or jolt during aerosolization. As a result, aerosolization efficiency will be affected. Moreover, components of the aerosol generating apparatus 10 may be more prone to damage and wear if the position of the liquid container 20 and the adaptor 30 is not maintained.

A driving element 40 is accommodated by the adaptor 30. The driving element includes a piezoelectric (PZT) element (404, not shown) and a substrate 402. The substrate 402 may be flat or with a projection. The substrate 402 is made of metal or any kind of material suitable for prolonged vibration without breakage. The PZT element 404 is coupled to the liquid outlet side of the substrate 402, and the liquid inlet side of the substrate 402 faces the membrane 204. When the liquid container 20 is engaged with the adaptor 30, the substrate 402 and the membrane 204 are in contact. During aerosolization, electric power is provided to the PZT element through electric contacts, such as wires or leads. As a result, the PZT element 404 vibrates and the vibration energy thereof is transmitted to the membrane 204 to aerosolize the liquid passing through. The adaptor 30 includes some additional structures/components to ensure that the positioning of the liquid container 20, the membrane 204 and the adaptor 30 are in a desired manner, e.g., aligned. Such additional structures/components will be discussed in the subsequent disclosure.

Figure 2:
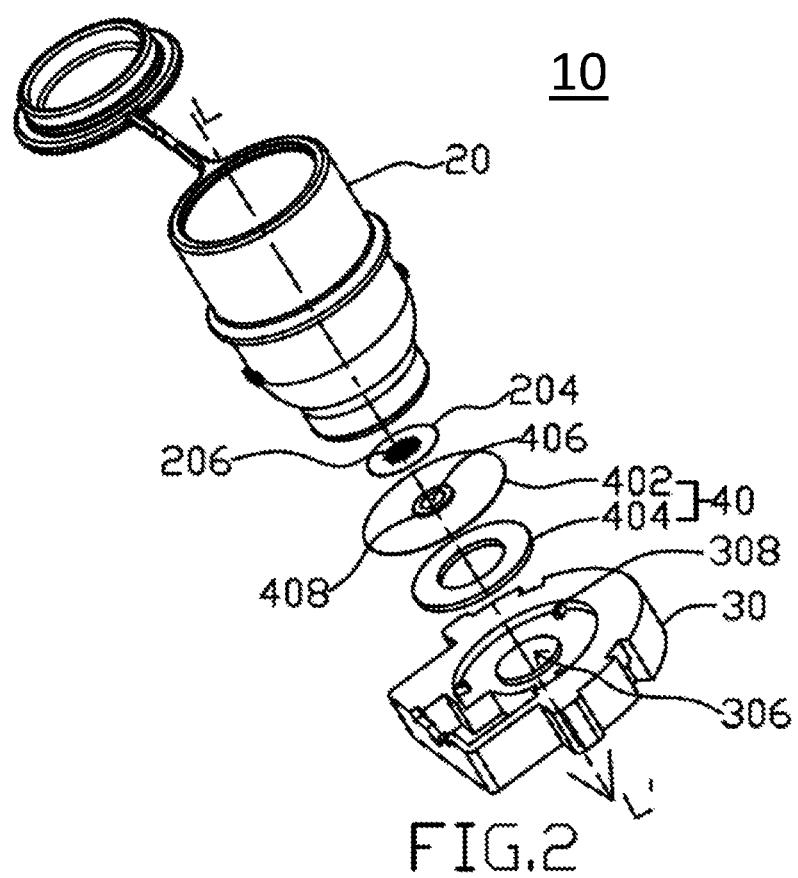

FIG. 2 illustrates an exploded view of an aerosol generating apparatus 10 according to some embodiments of the present disclosure. Liquid medicament travels from the liquid container 20 towards the adaptor 30 along the dotted line L-L'. The PZT element 404 is positioned at the liquid outlet side of the substrate 402. Alternatively, although not shown here, the PZT element 404 may be positioned at the liquid inlet side of the substrate 402 and face the liquid container 20. A distance/spacing between the PZT element 404 and the adaptor 30 is always maintained such that the vibration of the PZT element 404 will not be hindered by the adaptor 30.

In certain embodiments, the substrate 402 includes an aperture 406 at about its center. The aperture 406 corresponds to the location of the orifices 206 of the membrane 204 when the liquid container 20 is engaged with the adaptor 30. As such, liquid can be directed from the liquid container 20 through the substrate 402 via such aperture 406. Aerosolized liquid then leaves the substrate 402 through such aperture 406 and exits the adaptor 30 via its through hole 306.

In certain embodiments, the substrate 402 includes a projection 408 corresponding to the location of the aperture 406. In other words, substrate 402 is elevated at the projection 408, which becomes in contact with the membrane 204 when the liquid container 20 and the adaptor 30 are engaged. In some embodiments, only the projection 408 is in contact with the membrane 204 during aerosolization. The projection 408 may also serve to partially deform the membrane 204 when the liquid container 20 and the adaptor 30 are engaged. One example is to push the liquid container 20/membrane 204 against the substrate 402/projection 408. Aerosolization effect may be adjusted accordingly.

When the liquid container 20 and the adaptor 30 are engaged, the adaptor 30 is configured to contact the substrate's 40 periphery. The periphery of the substrate 40 shall be the outer perimeter of the substrate 40. In other words, it is the border area of the substrate 40 as distinguished from its internal regions or center. An example of the periphery of the substrate 40 is the ring region that marks the outer most boundary of the substrate 40. The adaptor 30 is configured to be in contact with the periphery of the substrate 402 for the purpose of minimizing hindrance against the vibration of the substrate 402 and for improving aerosolization efficiency. More particularly, the adaptor 30 is configured to make contact with only part of the periphery of the substrate 40.

Any contact of the substrate 402 with any element will create a hindered and/or dead spot during vibration, thus affecting vibration efficiency. It is preferred that the substrate 402 receives as little hindrance as possible. Moreover, hindrance from the periphery region of the substrates creates less energy loss than that from the more central regions. In the present disclosure, a jack 308 (or a means for supporting the substrate 402) is provided at the adaptor 30 to achieve the foregoing goal. That is, the jack 308 of the adaptor 30 makes contact with the substrate 402 only at a specific location of its periphery. Accordingly, there is only minimal contact between the adaptor 30 and the substrate 402. The jack 308 may be attached to the adaptor 30 or integrally formed with the adaptor 30.

The jack 308 further serves to ensure that the substrate 402 will be placed at a predetermined position for desired aerosolization. For example, the jack 308 may serve to align the adaptor 30 and the substrate 402. The resulting aerosol generating apparatus 10 may deliver more desired aerosolization with less energy consumption. Higher aerosolization efficiency may also lead to fewer blockages or clogging, thus prolongs the life of the aerosol generating apparatus 10. In some embodiments, the jack 308 is made of materials other than metal, such as polymer.

In certain embodiments, the adaptor 30 includes only one jack 308. The periphery of the substrate 402 may be mounted on and supported by such one jack 308 without adhesive. However, in the one jack 308 configuration, it is recommended that adhesive, e.g., glue, gel, hot molding or welding, is applied in order to maintain structural strength and integrity. Alternatively, the adaptor 30 may include more than one, e.g., two, three or more, jacks 308, that also correspond to the substrate's 402 periphery. Here, adhesive is optional between the plurality of jacks 308 and the substrate 402.

When engaged, the substrate 402 only makes contact with the tips of the plurality of jacks 308 at the periphery. Accordingly, only small areas of the periphery where the jacks 308 touch the substrate 402 may be affected during vibration. In other words, the adaptor 30 supports the substrate 402 just enough to maintain position during vibration/aerosolization, allowing substrate 402 to vibrate freely with minimal hindrance. In certain embodiments, this may be considered as the substrate 402 is partially supported by the adaptor 30. Such minimal hindrance provides an aerosol generating apparatus capable of delivering desired aerosolization with reduced energy consumption. It is important to note that the foregoing disclosure is only exemplary and shall not be considered as exhaustive. A person having ordinary skill in the art will understand that the configuration of any number of jacks 308 will fall within the scope of the present disclosure as long as the contact between the substrate 402 and the adaptor 30 is minimal. In a preferred embodiment, the adaptor 30 is only in contact with the periphery of the substrate 402 at no more than three locations, in the form of tip of a jack or any other readily known supporting structure.

The jack 308 further serves to lift and maintain the substrate 402 at a certain height, i.e., away from the liquid inlet surface of the adaptor 30. In other words, a space is maintained between the liquid inlet surface of the adaptor 30 and the substrate 402. Without such space, additional sections of the substrate 402 may come in contact with the adaptor 30 when vibrated, which results in vibration hindrance and loss. Moreover, such space serves to accommodate the PZT element 404 that couples to the substrate 402. The PZT element 404 is disposed at the liquid outlet surface of the substrate 402. Some space between the substrate 402 and the adaptor 30 should be preserved to prevent the PZT element 404 from contacting the adaptor 30. With such space maintained, vibration energy will not be reduced and vibration pattern of the substrate 402 will not be hindered.

Figure 3:
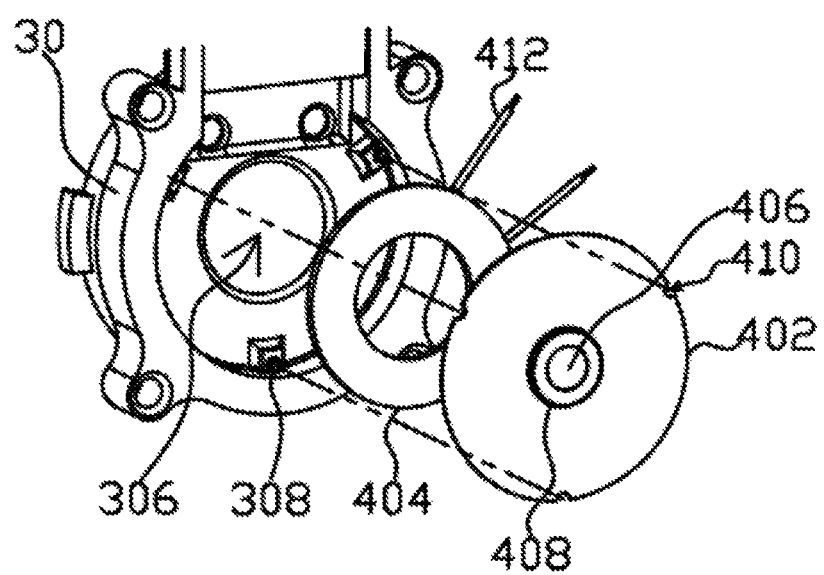

FIG. 3 is an exploded view of part of the aerosol generating device according to some embodiments of the present disclosure. In order to be better supported by the jacks 308, the substrate 402 may include mating structure 410 that corresponds to the jack 308. For example, the mating structure 410 may be an indention or recess corresponding to the shape of the jack 308. As a result, when engaged along the dotted lines, the substrate 402 is directed to a predetermined position where the mating structure 410 and the jack 308 match. Correspondingly, the aperture 406 may be directed to another predetermined position suitable for better aerosolization. Moreover, the substrate 402 may become fitted with the jack 308 such that horizontal movement during aerosolization is reduced or inhibited. In another example, the aperture 406 is then aligned with the through hole 306 of the adaptor such that aerosolized liquid can leave the adaptor 30 without obstruction. Again, there may be any numbers (one, two, three or more) of jack(s) 308 at the adaptor 30, and therefore there may be corresponding numbers of mating structure 410 at the substrate 402.

Here, the electric contact 412 of the PZT element 404 is illustrated. Such electric contact 412 may be leads or electric wires. It is configured to provide electric power to the PZT element 404 to create vibration. Such vibration is then transmitted to the membrane 204 through the substrate 402 for aerosolization. In general, the PZT element 404 is ring shaped so aerosolized liquid can pass through its central through hole. However, the shape of the PZT element 404 is not limited to circular and may be adjusted if needed. For example, the shape of the PZT element 404 may not be a complete ring. It can be C-shaped or an incomplete ring with gaps. As long as vibration energy can be transmitted from the periphery towards the center of the substrate 402, the PZT element 404 can be of any shape or form.

Figure 4A:
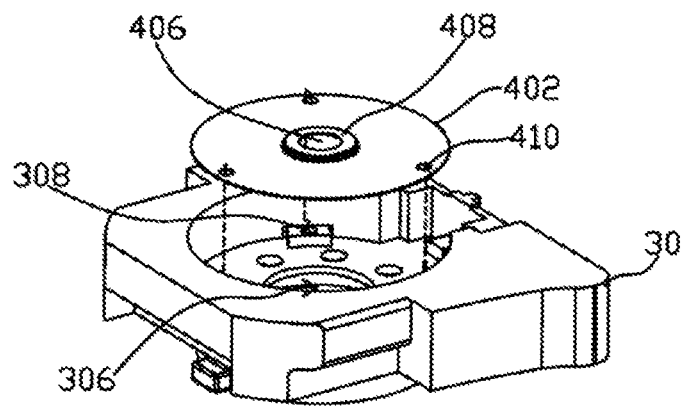
Figure 4B:
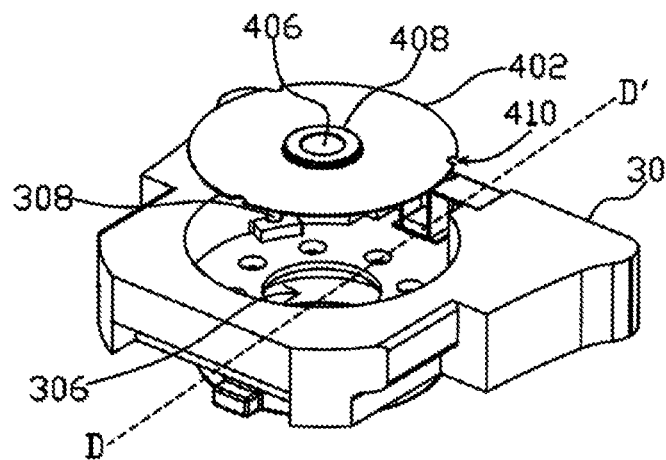
Figure 4C:
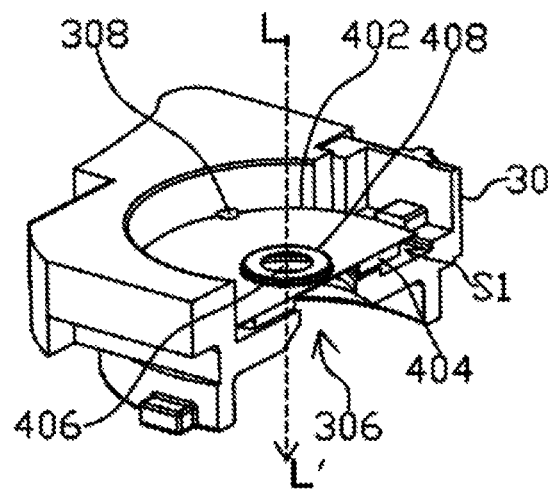

FIGS. 4A-4C are side views of part of an aerosol generating apparatus in accordance with some embodiments of the present disclosure.

In FIG. 4A shows the embodiment when the substrate 402 is not engaged with the adaptor 30. The aperture 406 is located substantially at the center of the substrate 402 and corresponds to the through hole 306 of the adaptor 30. As such, aerosolized liquid can exit the adaptor 30 without obstruction. The mating structure 410 is a puncture hole at the periphery of the substrate 402. Such mating structures 410 correspond to the jacks 308 of the adaptor 30. Accordingly, the substrate 402 is maintained at a predetermined position when the mating structure 410 is mated with the jack 308, i.e., when the substrate 402 is accommodated by the adaptor 30. In certain embodiments, the mating structure 410 may be a tab protruding out of the periphery of the substrate 402. In such embodiments, the corresponding supporting structure at the adaptor 30 would not be a jack or anything that protrudes out from the adaptor 30. Instead, it can be an indentation on the adaptor 30 to accommodate the protruding tab. It is to be noted that the number, structure, placement or configuration of the mating/supporting structure between the substrate 402 and the adaptor 30 should not be limited to only the embodiments disclosed herein. A person having ordinary skill in the art would understand that any mechanism that provides minimal contact between the substrate 402 and the adaptor 30 at the periphery of the substrate 402 should fall within the scope of this disclosure.

FIG. 4B shows another embodiment when the substrate 402 is not engaged with the adaptor 30. FIG. 4C shows the same embodiment when the substrate 402 is engaged with the adaptor 30. Particularly, FIG. 4C shows a cross-sectional view of the components along the dotted line D-D' in FIG. 4B but with the substrate 402 engaged with the adaptor 30. As illustrated, the substrate 402 is in contact with the adaptor 30 only at the jacks 308. In other words, except the jacks 308, the inner perimeter of the adaptor 30 surrounding the substrate 402 is not in contact with the substrate 402. Specifically, a space is formed and maintained between the substrate 402 and the adaptor 30 except where the jack 308 is. As such, there's limited or minimal hindrance against the vibration of the substrate 402 by the adaptor 30. The resulting driving element 40 generates desired vibration energy with less electric power consumption.

The liquid/aerosol flow direction from L to L' is again illustrated in FIG. 4C. The substrate 402 includes a first liquid inlet side facing the liquid container (not shown), and a first liquid outlet side facing the adaptor 30. Furthermore, the adaptor 30 includes a second liquid inlet side facing the liquid container (not shown) and a second liquid outlet side at the through hole 306 where aerosolized liquid leaves the adaptor 30. As illustrated, a space S1 is maintained between the first liquid outlet side and the second liquid inlet side such that the two sides will not touch each other during aerosolization. The space S1 also serves to ensure that there is enough room between the first liquid outlet side and the second liquid inlet side to accommodate the PZT element 404. A preferred design is to ensure that PZT element 404 do not contact the adaptor 30. Otherwise, vibration of the PZT element 404 will be hindered and aerosolization efficiency will be affected. In certain embodiments, an O-ring (not shown), which seals the PZT element 404 from exposure to the outside environment, is disposed between the first liquid outlet side and the second liquid inlet side. The O-ring is essentially a cushion, and the aforementioned two sides may be considered as indirectly in contact with each other. Because the O-ring is made of flexible material(s), the vibration of the PZT element 404 will not be hindered even with the O-ring in contact with both the first liquid outlet side and the second liquid inlet side. In other words, the space S1 may be occupied by the O-ring while the resulting aerosol generating apparatus 10 is still capable of delivering desired aerosolization efficiency.

Figure 5A:
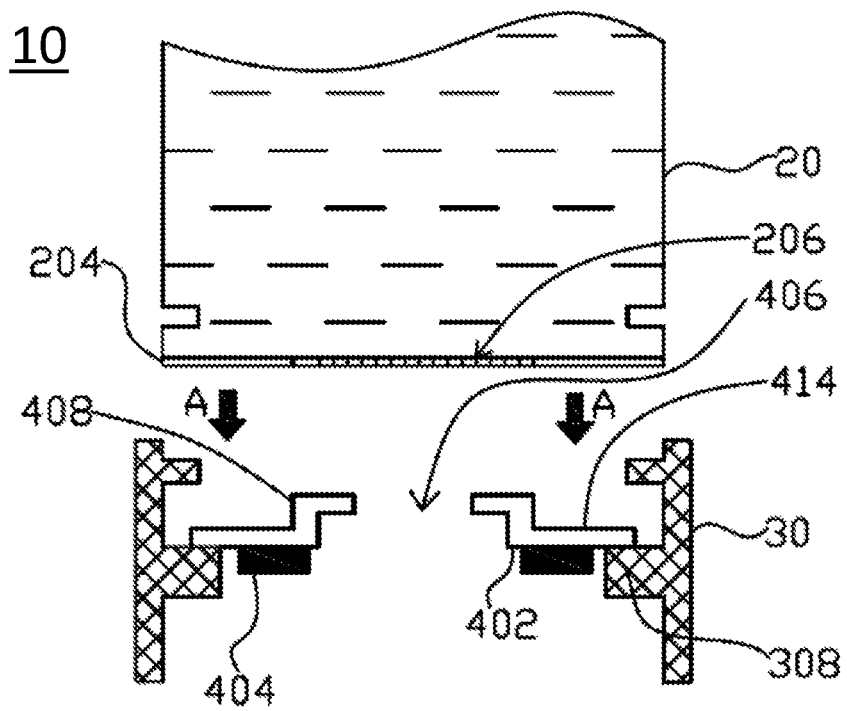
Figure 5B:
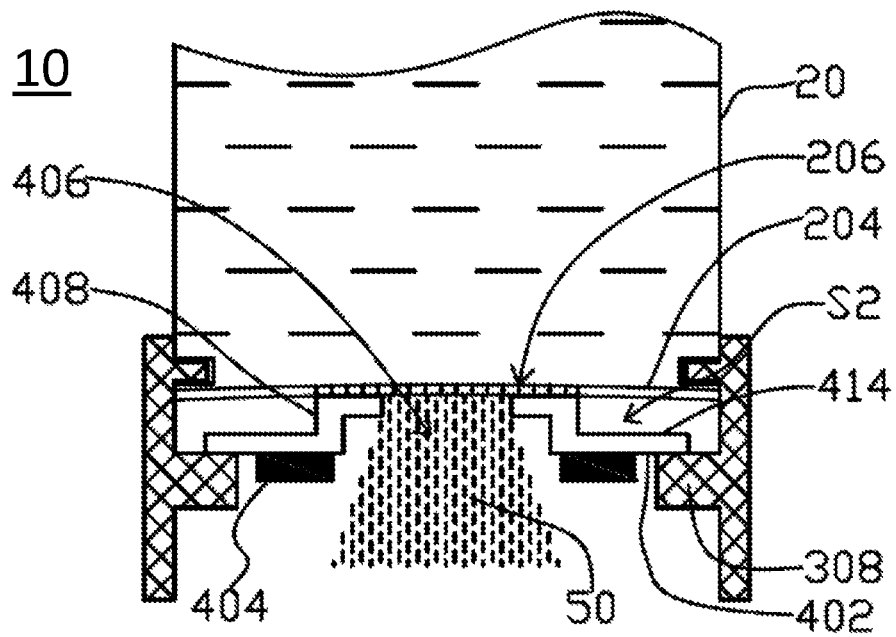

FIGS. 5A-5B are cross-sectional views of the aerosol generating apparatus according to some embodiments of the present disclosure.

FIG. 5A shows the aerosol generating apparatus 10 when the liquid container 20 is not engaged with the adaptor 30. One side of the liquid container 20 is affixed with the membrane 204, and the orifices 206 are located at or around the center of the membrane 204. The liquid container 20 is designed to engage the adaptor 30 in the direction indicated by the two arrows A. The adaptor 30 includes one or more jacks 308 to support the substrate 402. The one or more jacks 308 are so positioned that they only make contact with the periphery of the substrate 402. The substrate 402 may be supported by the one or more jacks 308 without adhesive. That is, the substrate 402 is not required to be permanently affixed to the one or more jacks 308. The engagement between the liquid container 20 and adaptor 30 may provide further stability as to the position of the substrate 402 during aerosolization. The foregoing will be discussed in the disclosure of FIG. 5B. Alternatively, the substrate 402 may be permanently secured to the one or more jacks 308 at its periphery. For example, gel, adhesive, hot molding or welding technique may be applied to permanently secure the substrate 402 with the jacks 308. The foregoing adhesive may be applied when extra accuracy and stability is needed for specific aerosol generating apparatuses.

In some embodiments, the substrate 402 includes a planar part 414 at its inlet surface extending annularly from the projection 408. The planar part 414 also surrounds the aperture 406, which penetrates the projection 408 of the substrate 402. The projection 408 substantially corresponds to the orifices 206 of the membrane 204, while the planar part 414 substantially corresponds to such portions of the membrane 204 without orifices.

FIG. 5B shows the aerosol generating apparatus 10 with the liquid container 20 and the adaptor 30 engaged. Here, electric power has been provided to the PZT element 404 for vibration and aerosol 50 is generated. The liquid container 20 is engaged with the adaptor 30. Particularly, when the foregoing two is engaged for aerosolization, the membrane 204 is in contact with the substrate 402. As such, vibration energy is transmitted from the substrate 402 to the liquid passing through the orifices 206 for aerosolization. In certain embodiments, the projection 408 of the substrate 402 is in contact with the membrane 204, but not the planar part 414. That it, a space S2 is maintained between the perforated membrane and the planar part. As a result, vibration energy is transmitted to the membrane 204 though the projection 408 only. Accordingly, vibration of the membrane 204 will not be hindered by the planar part 414 and is in free-form movement. Here, being in "free-form" or "free-form movement" means that the vibration of the membrane 204 is not affected by undesirable influences of surrounding component(s) or structure(s) of the aerosol generating apparatus. In addition "free-form" or "free-form movement" means that the membrane 204 is capable of reaching a resonance state corresponding to the vibration energy received from the projection 408. Hence, although certain section of the membrane 204 is in contact with and affected by the projection 408, the membrane 204 is in "free-form" or "free-form movement" as long as it's capable of resonating. The formation of the space S2 helps preserve the free-form movement of the membrane 204. As such, aerosolization efficiency is improved because energy from the PZT element 404 is more effectively transmitted to the membrane 204.

In some embodiments, when the liquid container 20 and the adaptor 30 are engaged, a pressing force from the liquid container 20 along a direction perpendicular to the substrate 402 is applied. As a result, the membrane 204 is pressed against the substrate 402 but not to the extent that the membrane 204 is punctured or deformed by the projection 408. In combination with the jacks 308, the substrate 402 is clamped by the liquid container 20 and the adaptor 30. Accordingly, the position of the substrate 402 relative to the adaptor 30 is aligned and maintained. Without the foregoing, the substrate 402 might shift or jolt during operation, which may lead to reduced aerosolization efficiency. Shifting or jolting of the substrate 402 may also cause damage and reduce the life of the aerosol generating apparatus. In certain embodiments, as illustrated in FIG. 5B, a certain degree of force is applied such that the membrane 204 is pressed upon by the projection 408. In other words, the membrane 204 becomes slightly concaved or curved. Vibration energy may be transmitted to the membrane 204, especially at the locations with orifices 206, in a more concentrated manner. The resulting vibration pattern or resonance state of the membrane 204 is more likely to reach a desired aerosolization efficiency. More force may be applied so as to create more deformation of the membrane 204 depending on specific needs, e.g., characteristic of the liquid medicament, required aerosolization efficiency, and so on.

Although not illustrated in FIG. 5B, the substrate 402 may include no projection 408 and therefore the planar part 414 is essentially the entire liquid inlet surface of the substrate 402. When the liquid container 20 and the adaptor 30 are engaged, the membrane 204 covers the substrate 402 entirely.

FIGS. 6A-6E are cross-sectional views of the aerosol generating apparatus in accordance with some embodiments of the present disclosure.

Figure 6A:
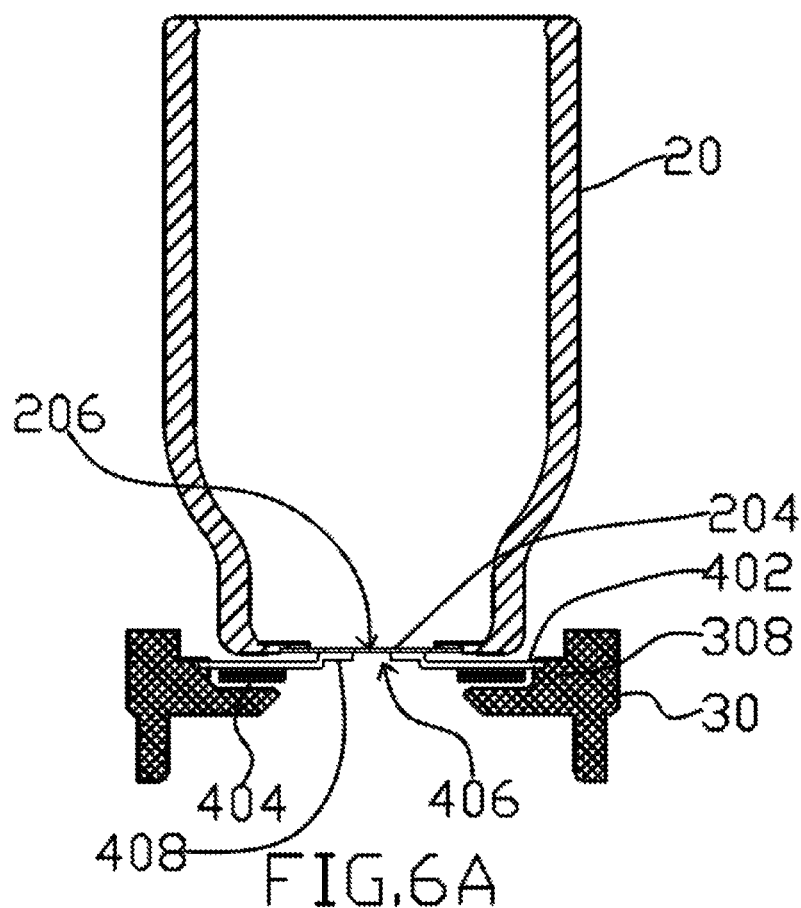

In FIG. 6A, the liquid container 20 is engaged with the adaptor 30. Here, an interface for mating/affixing the liquid container 20 to the adaptor 30 is omitted for clarity. The membrane 204 is in contact with the projection 408 of the substrate 402. The orifices 206 of the membrane 204 correspond to the aperture 406 and projection 408, which is at or around the center of the substrate 402. The substrate 402 is supported by the jack 308 of the adaptor 30. The force from the liquid container 20 pushes the substrate 402 against the jacks 308. Accordingly, the position of the substrate 402 is maintained when the liquid container 20 and the adaptor 30 are engaged. The foregoing ensures that the vertical and horizontal position of the substrate 204 relative to the adaptor 30 and the liquid container 20 will not be changed during aerosolization. In other words, the substrate 402 is considered to be clamped by the adaptor 30/jack 308 and the liquid container 20.

Figure 6B:
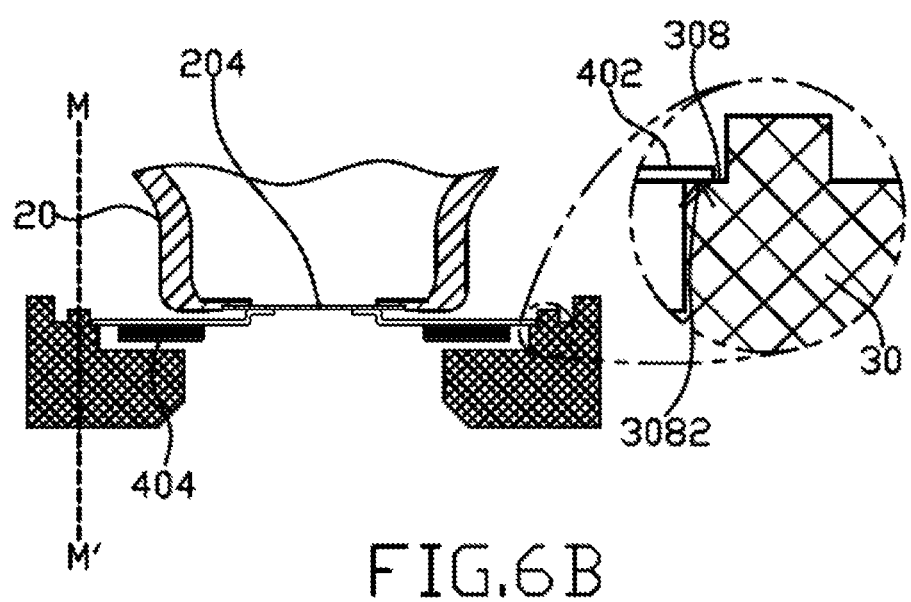

FIG. 6B illustrates a magnified view of one exemplary jack 308 of the adaptor 30. The jack 308 includes a first surface 3082 extending along a direction perpendicular to the longitudinal axis M-M' of the adaptor 30. When the substrate 402 is accommodated and supported by the jacks 308, the substrate 402 is mounted on the first surface 3082. In other words, the substrate 402 is supported by the first surface 3082. Adhesive, heat bonding, welding or other securing means may be applied between the substrate 402 and the first surface 3082. However, any form of adhesive shall be applied with caution because too much of it may obstruct the vibration of the substrate 402. Moreover, there is pressing force from the liquid container 20, and the substrate 402 is clamped by the jack 308 and the liquid container 20. As long as the position of the substrate 402 can be maintained during aerosolization, adhesive may not be needed.

Figure 6C:
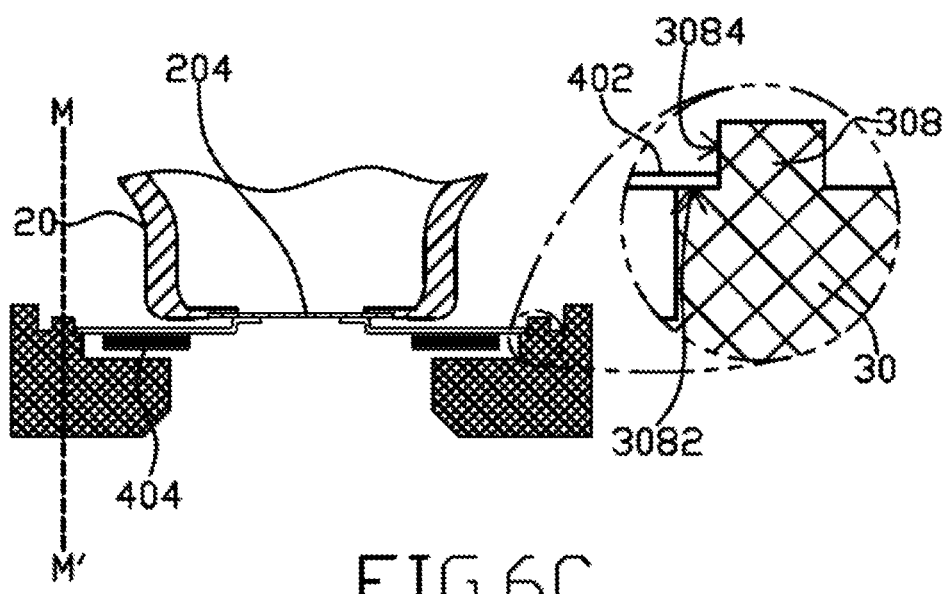

FIG. 6C illustrates a magnified view of another exemplary jack 308 of the adaptor 30. In addition to the first surface 3082, the jack 308 includes a second surface 3084 extending along the longitudinal axis M-M' of the adaptor 30. Here, the substrate 402 may be in contact with both the first and second surfaces 3082, 3084. Such configuration may serve to reduce the horizontal movement of the substrate 402 relative to the adaptor 30 during aerosolization. Moreover, the substrate 402 making contact with the second surface 3084 may lead to a more accurate alignment of the substrate 402 in respect to the liquid container 20. Particularly, the center of the substrate 402 is where vibration energy is the highest and therefore is a more desired location to interact with the membrane 204. As stated in the previous paragraph, adhesive may be optionally applied between the substrate 402 and the first and second surfaces 3082, 3084, based on specific needs.

Figure 6D:
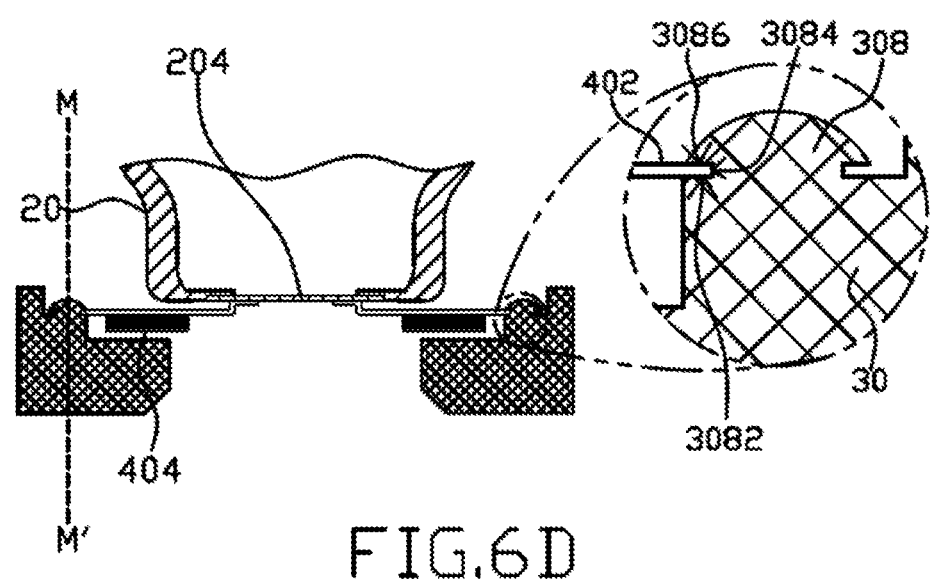

FIG. 6D illustrates a magnified view of yet another exemplary jack 308 of the adaptor 30. In addition to the first and second surfaces 3082, 3084, the jack 30 includes a third surface 3086. The third surface 3086 may be parallel to the first surface 3082 and is designed to contact the liquid inlet surface of the substrate 402. The jack 308 may be designed with the three surfaces. Alternatively, the distal part of the second surface 3084 may be melted using hot melting adhesive process, thus forming the third surface 3086 parallel to the first surface 3082. In some embodiments, the first and third surfaces 3082, 3086 clamp the substrate 402. Accordingly, the horizontal and vertical movement of the substrate 402 relative to the adaptor 30 may be reduced, allowing a more accurate alignment between the membrane 204 and the substrate 402. If even further alignment accuracy is desired, force may be applied from the liquid container 20 to the substrate 402 against the jacks 308. Additionally, adhesive may be applied between the substrate 402 and the jacks 308. Again, adhesive between the substrate 402 and the surfaces of the jack 308 is optional.

Figure 6E:
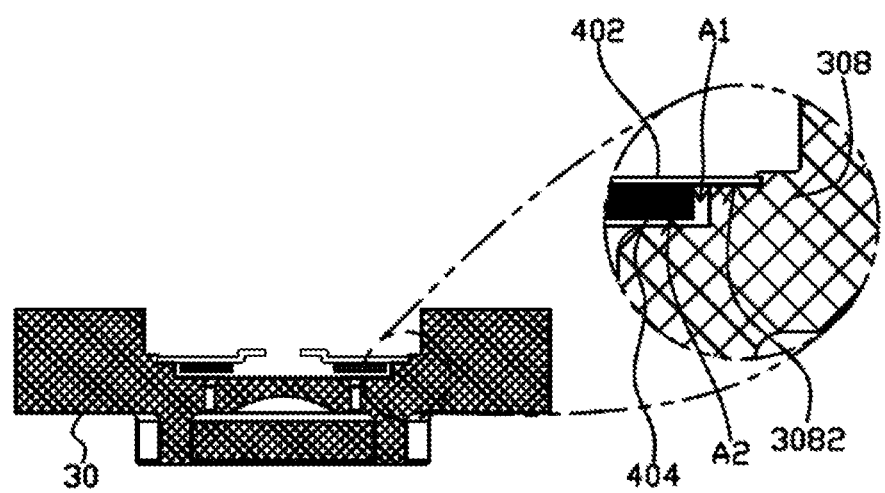

FIG. 6E illustrates a magnified view of yet another exemplary jack 308 of the adaptor 30. This embodiment, along with the ones in FIGS. 6A-6D, aim to emphasize that the size or configuration of the jack 308 shall not be limited by the disclosure herein. A person having ordinary skill in the art would understand that a jack 308 may be of any shape or form as long as the following are achieved: 1) that the substrate 402 can be supported by the jack 308; 2) that a space A1 is maintained between the PZT element 404 and the jack 308; 3) that a space A2 is maintained between the substrate 402/PZT element 404, and the adaptor 30; and 4) that there is minimal contact between the periphery of the substrate 402 and the adaptor 30/jack 308.

FIGS. 7A-7D are exemplary views of the substrate and the adaptor in accordance with some embodiments of the present disclosure.

Figure 7A:
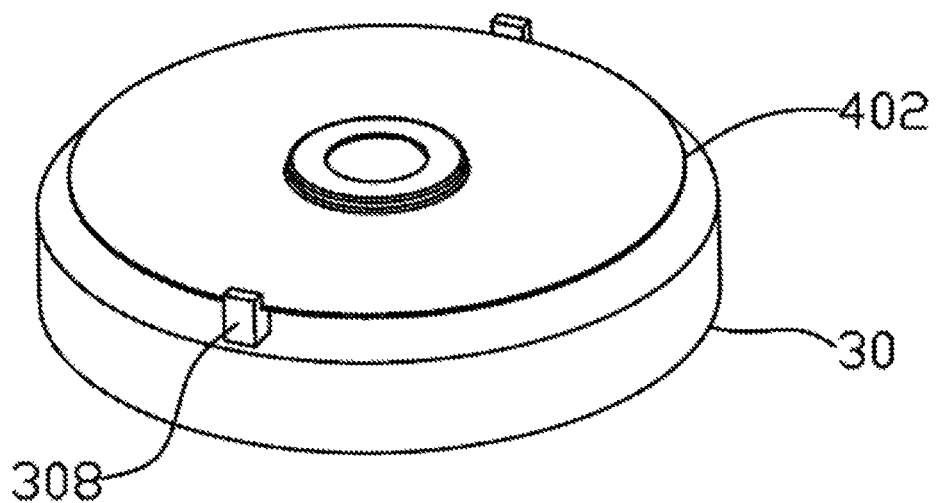

In FIG. 7A, the adaptor 30 includes two jacks 308. The jacks 308 may be positioned at two ends of the substrate 402's diameter. This figure shows that the jacks 308 are only in contact with the periphery of the substrate 402. Again, periphery means the outer most boundary of the substrate 402 that's away from its center. Vibration efficiency is the highest when the substrate 402 is supported by the jacks 308 only at the periphery and only with minimal contact. In other words, hindrance from the jacks 308 against the vibration of the substrate 402 is minimized. Still, the jacks 308 are so configured to ensure the substrate 402 is stably maintained.

Figure 7B:
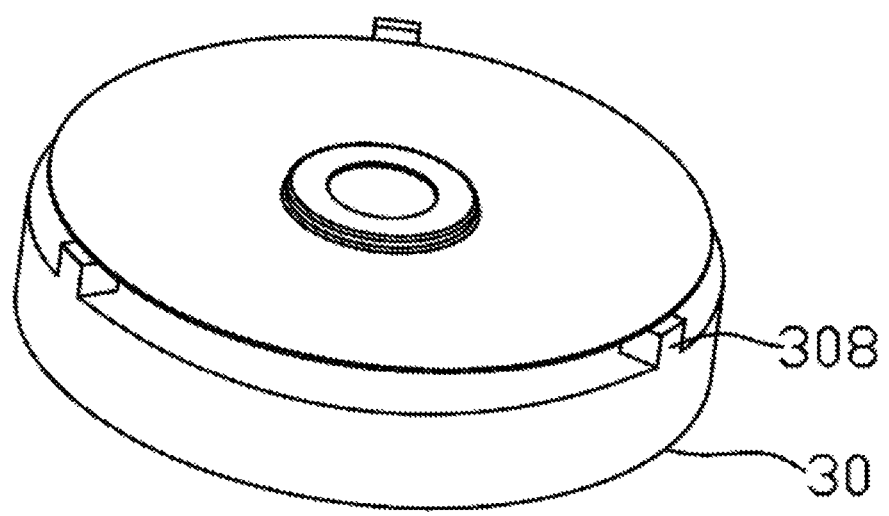

In FIG. 7B, the adaptor 30 includes three jacks 308. The three jacks 308 are evenly distributed around the periphery of the substrate 402. However, other distribution patterns of the jacks 308 are also applicable. The three jacks 308 may also have the same or different shapes, based on specific needs. For example, as illustrated in FIG. 7B, at least one of the three jacks 308 has a lower height than the others.

Figure 7C:
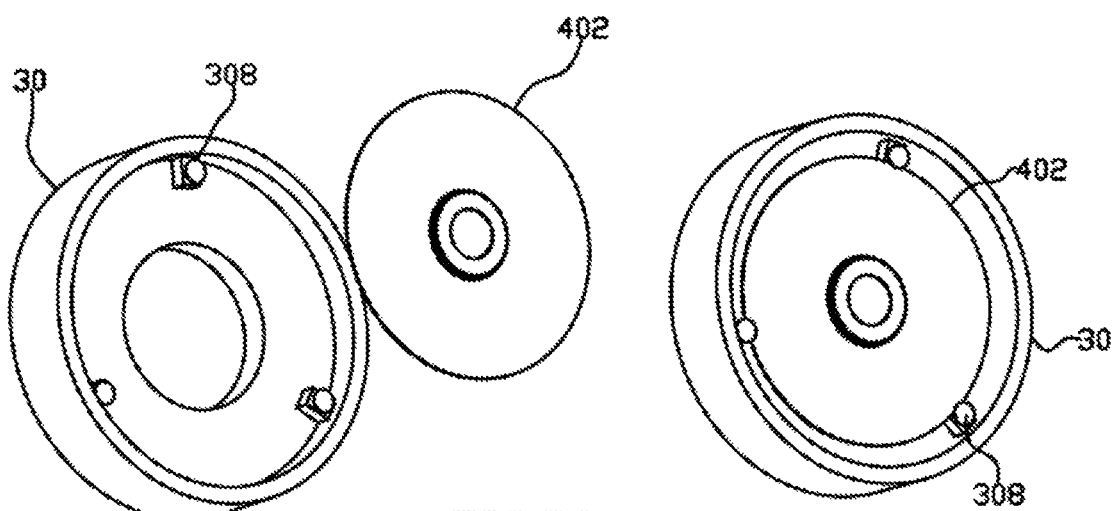

FIG. 7C shows the substrate 402 and the adaptor 30 before and after engagement according to some embodiments. Here, the jack 308 has as shape of a bolt. As illustrated, after engagement, the bolt head of the jacks 308 partially covers the periphery of the substrate 402. This may be achieved by using flexible and/or malleable material(s) for the jacks 308. During assembly, the periphery of the substrate 402 is pressed down against the jacks 308 so as to partially deform them. After the substrate 402 reaches a desired position, such as mated with a groove under the bolt head of the jacks 308, the jacks 308 return to their original shape. It can be understood that the jacks 308 now clamps on the periphery of the substrate 402. As a result, the substrate 402 is supported by the jacks 308, and the relative position between the substrate 402 and the adaptor 30 will be maintained.

Figure 7D:
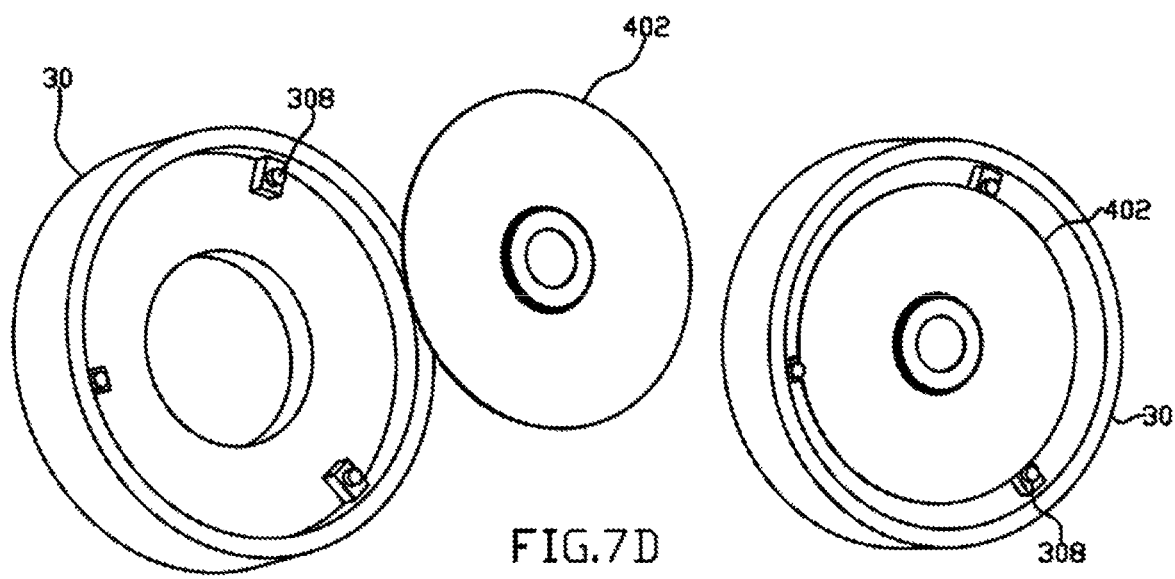

FIG. 7D shows the substrate 402 and the adaptor 30 before and after engagement according to some other embodiments. Here, the jacks 308 are in the form of a combination of cuboid and column. When engaged, both the cuboid and column are in contact with the substrate 402. Particularly, the cuboid is configured to support the substrate 402, and the column is configured to restrict horizontal movement of the substrate 402.

The embodiments in FIGS. 7A-7D shows that the jacks 308 may be of any shape, size, form, configuration or combination(s) thereof of as long as the following are achieved: 1) that the substrate 402 can be supported by the jack 308; 2) that there is minimal relative movement between the adaptor 30 and the substrate 402 after the liquid container 20 is engaged with the adaptor 30; and 3) that there is minimal contact between the periphery of the substrate 402 and the adaptor 30/jack 308.

FIGS. 7A-7D also show that only a very small area of the periphery of the substrate 402 is in contact with the jacks 308. In some embodiments, no more than six percent of the surface area of the substrate 402 is in contact with the jacks 308. In certain embodiments, multiple jacks 308 are in contact with approximately two percent of the surface area of the substrate 402. In yet some other embodiments, each jack 308 is in contact with around two percent of the surface area of the substrate 402. Only small areas of the substrate 402 make contact with the adaptor 30. As such, vibration from the PZT element 404 can be transmitted to the membrane 204 through the substrate 402 more efficiently. Also, due to such minimal contacts, it is easy to remove the substrate 402 from the adaptor 30. Users may replace used or damaged substrate 402 or other components of the aerosol generating apparatus 10 more easily.

The present disclosure provides an aerosol generating apparatus having a liquid source and an adaptor. The liquid source includes a perforated membrane at one side facing the adaptor. Liquid medicament is provided from the liquid source to the adaptor through the perforated membrane. The adaptor includes an interface to mate with the liquid source. The adaptor further accommodates a driving element, which includes a piezoelectric element and a substrate. The periphery of the substrate is in contact with the adaptor through its supporting means. The supporting means is configured to form a space between the substrate and the adaptor when the adaptor is engaged with the liquid source. An aperture is provided at or around the center of the substrate, which corresponds to the perforated membrane. When provided with electric energy, the piezoelectric element vibrates. Such vibration energy is transmitted to the perforated membrane through the substrate for aerosolization. Because the supporting means are configured to contact only a very small area of the periphery of the substrate, hindrance to vibration is minimized. As such, the improved aerosol generating apparatus can generate a desired aerosolization result with less energy consumption.

Although the present disclosure and its advantages have been described in detail, it should be understood that various changes, substitutions and alterations can be made herein without departing from the spirit and scope of the disclosure as defined by the appended claims. For example, many of the processes discussed above can be implemented in different methodologies and replaced by other processes, or a combination thereof.

Moreover, the scope of the present application is not intended to be limited to the particular embodiments of the process, machine, manufacture, composition of matter, means, methods and steps described in the specification. As one of ordinary skill in the art will readily appreciate from the disclosure of the present disclosure, processes, machines, manufacture, compositions of matter, means, methods, or steps, presently existing or later to be developed, that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

LISTING OF ELEMENTS aerosol generating apparatus 10
liquid container 20
lid 202
membrane 204
orifice 206
adaptor 30
body 302
interface 304
through hole 306
jack 308
first surface 3082
second surface 3084
third surface 3086 driving element 40
substrate 402
PZT element 404
aperture 406
projection 408
mating structure 410
electric contact 412
planar part 414
aerosol 50
space S1
space S2
space A1
space A2

What is claimed is:

1. An aerosol generating apparatus comprising:
    a liquid container including a perforated membrane through which a liquid can pass through;
    an adaptor configured to be detachably engaged with the liquid container; and
    a driving element including a piezoelectric element coupled to a substrate, wherein the adaptor is formed to operatively receive the driving element therein such that the driving element is aligned with the adaptor, and the substrate includes an aperture that positionally corresponds to the perforated membrane when the liquid container and the adaptor are engaged,
    wherein the aperture is aligned with a longitudinal center of the substrate,
    wherein the adaptor is configured to contact at least two predetermined locations on a periphery of the substrate, and includes at least two spaced-apart jacks for directly contacting the predetermined location on the periphery of the substrate,
    wherein each of the at least two jacks comprises a first surface that extends along a direction perpendicular to the longitudinal axis of the adaptor such that the predetermined location on the periphery of the substrate sits on and is in contact with the first surface,
    wherein the substrate includes an upper surface facing the perforated membrane and an opposite lower surface, the lower surface being in direct contact with the first surface of the at least two jacks at the predetermined location on the periphery of the substrate and the substrate is maintained at a predetermined distance away from an inner surface of the adaptor when the substrate sits on the at least two jacks, and
    wherein the adaptor and the driving element are operatively positioned relative to the liquid container such that the liquid flows in a first direction from the liquid container to the adaptor for aerosolization, and through the substrate.

2. The aerosol generating apparatus according to claim 1, wherein the first direction is parallel to the longitudinal axis of the adaptor.

3. The aerosol generating apparatus according to claim 1, wherein the predetermined location on the periphery of the substrate is adhered to the at least one jack.

4. The aerosol generating apparatus according to claim 1, each of the at least two jacks further comprises a second surface extending along the longitudinal axis of the adaptor such that the predetermined locations on the periphery of the substrate are in contact with respective ones of both the first and the second surfaces of the at least two jacks, and the substrate is maintained in horizontal alignment with the adaptor.

5. The aerosol generating apparatus according to claim 1, wherein only the predetermined location on the periphery of the substrate are fixedly supported by respective ones of the at least two jacks.

6. The aerosol generating apparatus according to claim 1, wherein the substrate includes a first liquid inlet side and a first liquid outlet side, and the adaptor includes a second liquid inlet side and a second liquid outlet side, wherein a space is maintained between the first liquid outlet side and the second liquid inlet side.

7. The aerosol generating apparatus according to claim 1, wherein the adaptor includes three or more jacks for directly contacting corresponding ones of a plurality of predetermined locations on the periphery of the substrate and maintaining the substrate at the predetermined distance from the inner surface of the adaptor.

8. The aerosol generating apparatus according to claim 1, wherein the substrate is made of metal and the jack of the adaptor is made of material other than metal.

9. The aerosol generating apparatus according to claim 1, wherein the adaptor comprises at least one electrical contact for providing electrical power to the piezoelectric element.

10. The aerosol generating apparatus according to claim 1, wherein the predetermined location on the periphery of the substrate is formed such that no more than six percent of a lower surface of the substrate is in direct contact with the adaptor.

11. The aerosol generating apparatus according to claim 1, wherein the piezoelectric element is a circular ring.

12. The aerosol generating apparatus according to claim 1, wherein the adaptor is configured with no more than three jacks, and the substrate is formed with no more than three predetermined locations on the periphery positionally corresponding to the no more than three jacks such that the substrate directly contacts only the no more than three jacks via the no more than three predetermined locations on the periphery, respectively.

13. The aerosol generating apparatus according to claim 12, wherein the adaptor and the substrate are maintained at the predetermined distance and in horizontal alignment when the no more than three jacks of the adaptor positionally directly contact the no more than three predetermined locations on the periphery of the substrate.

14. The aerosol generating apparatus according to claim 1, wherein the aperture of the substrate includes a projection formed at a liquid inlet surface thereof,
    wherein the perforated membrane is in contact with the projection when the liquid container is engaged with the adaptor.

15. The aerosol generating apparatus according to claim 14, wherein a pressing force in a direction perpendicular to the substrate is provided by the membrane against the projection such that position of the substrate relative to the adaptor is maintained.

16. The aerosol generating apparatus according to claim 14, wherein the substrate further includes a planar part at the liquid inlet surface extending away from the projection, and
    wherein when the liquid container is engaged with the adaptor, a space is maintained between the perforated membrane and the planar part.

17. An aerosol generating apparatus comprising:
    a liquid source with a perforated membrane through which a liquid can pass through;
    an adaptor detachably engaged with the liquid container, and the adaptor includes an interface configured to receive the liquid source; and a driving element operatively connectable to the adaptor and including a piezoelectric element and a substrate, the substrate including an aperture positionally aligned with a center of the substrate that corresponds to the perforated membrane when the liquid container and the adaptor are engaged, wherein the adaptor further includes at least one extension for supporting a predetermined location on a periphery of the substrate, wherein the at least one supporting extension includes a first surface, the first surface extending along a direction perpendicular to a longitudinal axis of the adaptor, wherein the substrate includes an upper surface facing the membrane and an opposite lower surface, wherein the lower surface is in direct contact only with the first surface of the at least one supporting extension and the substrate is maintained at a predetermined distance from an inner surface of the adaptor when the substrate sits on the supporting extension, wherein a liquid flow direction is defined as from the upper surface to the lower surface, wherein the substrate sits on the first surface along the liquid flow direction, and wherein when provided with electric power, the piezoelectric element vibrates the perforated membrane, through which the liquid passes and aerosolizes.

18. An aerosol generating apparatus comprising:
a liquid container including a perforated membrane through which a liquid can pass through;
an adaptor configured to be detachably engaged with the liquid container; and
a driving element including a piezoelectric element coupled to a substrate, wherein the driving element is operatively connectable to the adaptor, and the substrate includes an aperture positionally aligned with the perforated membrane when the liquid container and the adaptor are engaged, wherein the aperture is aligned with the center of the substrate, and the adaptor is configured to contact the substrate, wherein the adaptor includes at least one jack for directly contacting only a predetermined location on a periphery of the substrate, wherein the at least one jack further comprises a first surface, and the first surface extends along a direction perpendicular to a longitudinal axis of the adaptor such that the predetermined location on the periphery of the substrate sits on and is in contact only with the first surface, wherein the substrate includes an upper surface facing the membrane and an opposite lower surface, wherein predetermined location on the periphery at the lower surface of the substrate is in direct contact only with the first surface while the lower surface is maintained at a predetermined distance from an inner surface of the adaptor when the substrate sits on the at least one jack, and wherein during operation the aerosol generating apparatus is held upright where the liquid enters the perforated membrane from an inlet surface of the perforated membrane and exits the perforated membrane from an outlet surface of the perforated membrane due to gravity, and the substrate is positionally aligned with the adaptor via the at least one jack during operation.

* * * * *